United States Patent [19]

Apple

[11] Patent Number: 5,311,872
[45] Date of Patent: May 17, 1994

[54] PERIPHERAL ARTERIAL MONITORING INSTRUMENTS

[75] Inventor: Howard P. Apple, Highland Park, N.J.

[73] Assignee: Critikon, Inc., Tampa, Fla.

[21] Appl. No.: 36,797

[22] Filed: Mar. 25, 1993

Related U.S. Application Data

[62] Division of Ser. No. 823,909, Jan. 22, 1992, Pat. No. 5,218,968, which is a division of Ser. No. 453,519, Dec. 20, 1989, Pat. No. 5,103,833.

[51] Int. Cl.⁵ .................................................. A61B 5/02
[52] U.S. Cl. ................................. 128/687; 128/680; 128/694
[58] Field of Search .......................... 128/680-683, 128/687, 691, 694, 672, 677

[56] References Cited

U.S. PATENT DOCUMENTS

| | | |
|---|---|---|
| 3,903,872 | 9/1975 | Link . |
| 4,009,709 | 3/1977 | Link et al. . |
| 4,154,238 | 5/1979 | Link . |
| 4,174,707 | 11/1979 | Link et al. . |
| 4,349,034 | 9/1982 | Ramsey, III . |
| 4,360,029 | 11/1982 | Ramsey, III . |
| 4,367,751 | 1/1983 | Link et al. . |
| 4,469,099 | 9/1984 | McEwen ............................ 128/682 |
| 4,475,554 | 10/1984 | Hyndman . |
| 4,539,997 | 9/1985 | Wesseling et al. . |
| 4,564,020 | 1/1986 | Link . |
| 4,587,974 | 5/1986 | Link . |
| 4,651,747 | 3/1987 | Link . |
| 4,664,126 | 5/1987 | Link . |
| 4,697,596 | 10/1987 | Link . |
| 4,699,151 | 10/1987 | Link . |
| 4,699,152 | 10/1987 | Link . |
| 4,712,563 | 12/1987 | Link . |
| 4,718,428 | 1/1988 | Russell . |
| 4,727,884 | 3/1988 | Link . |
| 4,771,792 | 9/1988 | Seale . |
| 4,846,189 | 7/1989 | Sun . |
| 4,869,261 | 9/1989 | Penaz . |
| 4,984,577 | 1/1991 | Frankenreiter . |
| 5,089,961 | 2/1992 | Coble et al. . |
| 5,090,417 | 2/1992 | Mollan et al. . |
| 5,101,828 | 4/1992 | Welkowitz et al. . |
| 5,103,833 | 4/1992 | Apple ................................ 128/687 |
| 5,197,478 | 3/1993 | Souma ............................... 128/682 |
| 5,218,968 | 6/1993 | Apple ................................ 128/687 |

Primary Examiner—Lee S. Cohen
Assistant Examiner—Krista M. Pfaffle
Attorney, Agent, or Firm—Paul A. Coletti

[57] ABSTRACT

A method and apparatus are described for determining characteristics of peripheral arterial volume and compliance. A blood pressure cuff is inflated and deflated around a limb of the body and pressure measurements are taken. The volume of air removed from the cuff is determined in a quantifiable manner, such as by expelling air through an orifice of known characteristics or by means of a volume of know characteristics. The detected pressures and volume of air, removed are used to compute oscillation volume, which in turn is used to display arterial capacity and compliance as a function of transmural pressure and time. Arterial capacity may be displayed in terms of arterial radius, arterial cross-sectional area, or arterial volume. A display of these characteristics as a function of pre and post anesthetic administration is particularly useful to the anesthesiologist and surgeon.

13 Claims, 7 Drawing Sheets

PERIPHERAL ARTERIAL MONITORING INSTRUMENTS

This is a division of Ser. No. 823,909 filed Jan. 22, 1992, now U.S. Pat. No. 5,218,968, which is a division of application Ser. No. 453,519,filed Dec. 20, 1989, now U.S. Pat. No. 5,103,833 both of which are hereby incorporated by reference.

BACKGROUND OF THE INVENTION

This invention relates to monitoring instruments which provide information concerning peripheral vasculature and, in particular, to the use of such instruments to provide medical diagnostic information concerning arterial volume, cross-sectional area, and compliance.

FIELD OF THE INVENTION

The medical conditions of arteriosclerosis and hypertension are potentially debilitating and often life-threatening conditions which require early diagnosis and treatment. These conditions are characterized by changes in arterial blood flow volumes and rates and the response of arterial tissue to changes in blood pressure. A physiological phenomenon which plays a part in these arterial characteristics is referred to herein as arterial compliance, the ability of vasculature to respond to changes in these conditions. The arterial walls of the body include collagen, giving the walls the ability to expand and contract, and muscle tissue which in part controls this expansion and contraction. Vascular compliance includes the response of collagen and muscle in arterial walls to changing conditions. In addition, the condition of arteriosclerosis is characterized by the buildup of fatty substances along arterial walls. These substances can occlude the artery, and can impede the ability of the arterial walls to respond to changing conditions of blood pressure. The fatty substances characteristic of arteriosclerosis are thus a further factor governing arterial compliance. It is thus desirable to be able to analytically understand arterial volume and compliance when diagnosing or treating the medical conditions of hypertension and arteriosclerosis.

An understanding of a patient's arterial volume and compliance is also beneficial when administering anesthesia. The quantity of anesthetic administered to a patient should be just sufficient to eliminate a physiological response by the patient during surgery. If an insufficient amount of anesthetic has been administered, the cardiovascular system will respond reflexively when the patient is intubated prior to surgery. This response can be detected by monitoring arterial volume and compliance, and noting any reduction in these characteristics during intubation. A cardiovascular response can also be detected at the time of the first surgical incision, when an insufficient anesthetic will again be evidenced by a reduction in arterial compliance or volume. Thus, a surgical patient would benefit from the monitoring of arterial volume and compliance by the anesthesiologist and surgeon.

DESCRIPTION OF THE PRIOR ART

The significance of arterial volume and compliance has been recognized in the prior art. In a sequence of patents including U.S. Pat. Nos. 3,903,872; 4,565,020; 4,651,747; and 4,712,563 issued to William T. Link, methods and apparatus are described for calculating measurements of arterial volume and compliance. Link's technique as described in these patents involves taking a series of standard oscillometric blood pressure measurements. The first time derivative of the measured cuff pressure pulse, dP, at a time t within a patient's actual blood pressure pulse as a function of applied cuff pressure is then calculated to inferentially determine arterial volumetric changes $\Delta V$. As Link shows, this first derivative corresponds to changes in arterial volume changes $\Delta V$. A curve plotted from these calculations is transformed by Link to a curve of volumetric change as a function of transmural pressure, V/P, and this curve may in turn be differentiated to obtain a compliance curve $\Delta V/\Delta P$.

In a second sequence of patents including U.S. Pat. Nos. 4,664,126; 4,697,596; 4,699,151; and 4,699,152, Link extends this analysis to a technique in which the peak to peak amplitude of each cuff pulse and the patient's diastolic and systolic pressures are used to calculate a particular patient's own volumetric and compliance curves. Again, the volumetric and pressure information is determined inferentially from arterial pressure pulse information. The volumetric and pressure curves are used by Link in the determination of systolic, diastolic, and mean arterial blood pressure. The Link technique utilizes a ramp-up method of measuring pressure pulses, wherein pulse data is taken during inflation of a blood pressure cuff. The currently preferred technique for taking such measurements, which is incrementally deflating a blood pressure cuff from a pressure level in excess of systolic pressure and taking measurements over a range of declining pressure steps, is described in U.S. Pat. Nos. 4,349,034 and 4,360,029, issued to Maynard Ramsey, III.

A display of information concerning arterial volume which is useful to the anesthesiologist, surgeon or diagnostician is a curve representing arterial volume (in cc) or area (in $mm^2$) as a function of transmural pressure (in mm Hg). At a given point on the positive pressure side of this curve the volume or area may be represented by a value R, the effective arterial radius. The slope of the curve at any given point, $dV/dP$, represents arterial compliance, and a plot of $dV/dP$ as a function of transmural pressure represents the arterial compliance curve. In accordance with the principles of the present invention, the patient's arterial volume and compliance is represented in this format and, in correspondence thereto, the value of R over time is calculated and displayed. The display of this data provides the anesthesiologist with information concerning the patient's arterial volume and compliance characteristics, and also provides information as to changes occurring in arterial volume over time. This will enable the anesthesiologist to detect any response of the cardiovascular system to intubation or incision during a surgical procedure, thereby facilitating the correct delivery of anesthetic to the patient.

A display as described above may be further enhanced by providing the arterial compliance $dV/dP$ at a given transmural pressure for a patient undergoing diagnosis :r monitoring. The maximum value of $dV/dP$, referred to as peak arterial compliance, can also be ascertained from this information. A further display of this information which would be of use to a clinician would be a representation of arterial capacity, R, in relation to the circumference of the limb at which the blood pressure cuff of the monitoring instrument is attached.

In accordance with another aspect of the present invention, a variation of this display format provides a display of the patient's arterial volume data prior to the initiation of any surgical intervention and, in correspondence therewith, a current display of arterial volume data as the surgical intervention proceeds. Comparison of the data informs the anesthesiologist of the cardiovascular system response to bodily stimuli during the procedure.

A recent proposal relating to the determination of vascular compliance is known as the "Hartsafe Product Concept." In this procedure a pressure cuff is strapped to a patient's calf and inflated. When the cuff pressure attains a level of 70 Mm Hg, a calibration step is initiated by injecting one ml of air into the cuff. The system measures the change in pressure resulting from this quantified injection and calculates a calibration factor based upon the change. Cuff inflation continues and volume pulse signals are recorded until a minimal volume pulse signal or a maximum pressure value of 225 Mm Hg is attained. The system then commences a step deflate sequence. At individual pressure decrement steps of 10 Mm Hg the volume pulse signal is recorded. The sequence continues until a minimal pressure level is attained, at which time data acquision is complete. The system then performs "signal conditioning" using the volume pulse and cuff pressure signals at each 10 mm Hg cuff pressure decrement, and the calibrate signal previously stored. The volume-pressure curve, peak compliance, and other parameters are obtained by this "signal conditioning." The "Hartsafe" approach seems to be a more direct measurement of arterial volume than the Link techniques, in which arterial volume is calculated premised upon its relationship to the arterial pressure pulses, because an actual measurement of system response to a known change in cuff volume is taken during the calibration step of "Hartsafe." But the actual data which is computed for the volume-pressure curve appears to be similarly inferential, however, as the single calibration volume measurement is the only volumetric measure used in conjunction with the pulse signals to inferentially calculate the curve.

SUMMARY OF THE INVENTION

It would be desirable to provide arterial volume and compliance information that is based upon direct measurements of arterial volume and changes in arterial volume. It would further be desirable to continually recalibrate the system during the acquisition of such volumetric data, or to obviate the need for calibration entirely by obtaining highly accurate volumetric data in the first instance. In accordance with a further aspect of the present invention, a system for measuring arterial cross-section and compliance is provided in which a pressure cuff on a peripheral part of the body is inflated to a pressure level which occludes arterial vessels. The cuff is then deflated, and pressure measurements taken in correspondence with decreasing pressure levels. Air which is expelled during deflation is removed from the cuff through means for determining the volume of air expelled. This means may comprise, for instance, an orifice or transfer volume of known characteristics, or a flow measurement device. At each point at which a pressure determination is made, the volume of air removed from the cuff is precisely known, or is calculated based upon an immediately obtained volumetric calibration. Thus, there is no need for the use of a calibration factor or reliance upon a single prior calibration step in the determination of arterial volume and compliance performed by the system.

As air is removed from the pressure cuff in accordance with the present invention, the oscillation pressure peaks and changes in cuff volume as a function of pressure are recorded over a range of cuff pressures. From this information the oscillation volume is calculated. From the knowledge of oscillation volume measurements over the range of cuff pressures and conventional determination of systolic and diastolic pressure levels, the patient's arterial volume and compliance curves are reconstructed. Thus, accurate and complete information concerning blood pressure and arterial volume, cross-section and compliance in relation to transmural pressure and/or time is provided to the physician for monitoring and diagnosis.

DESCRIPTION OF THE PREFERRED EMBODIMENTS

Figure 1:
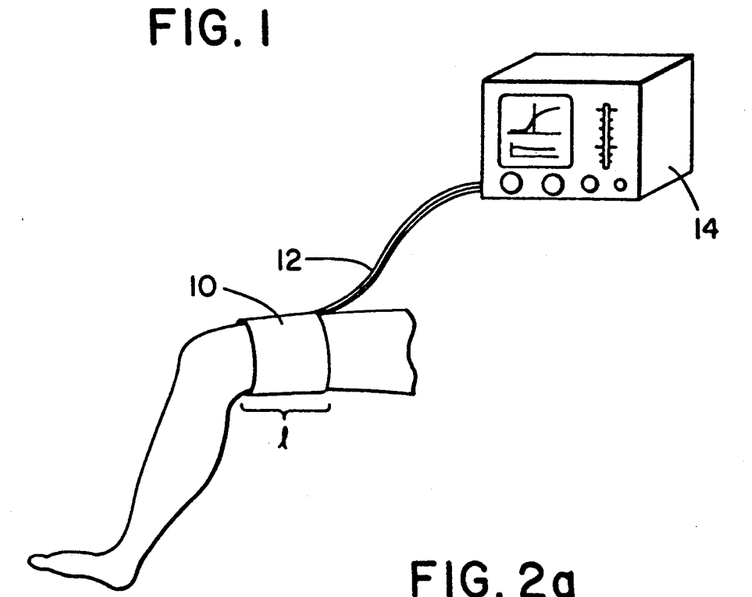
FIG. 1 illustrates a peripheral arterial monitoring instrument of the present invention attached to the thigh of the body.
Figure 2A:
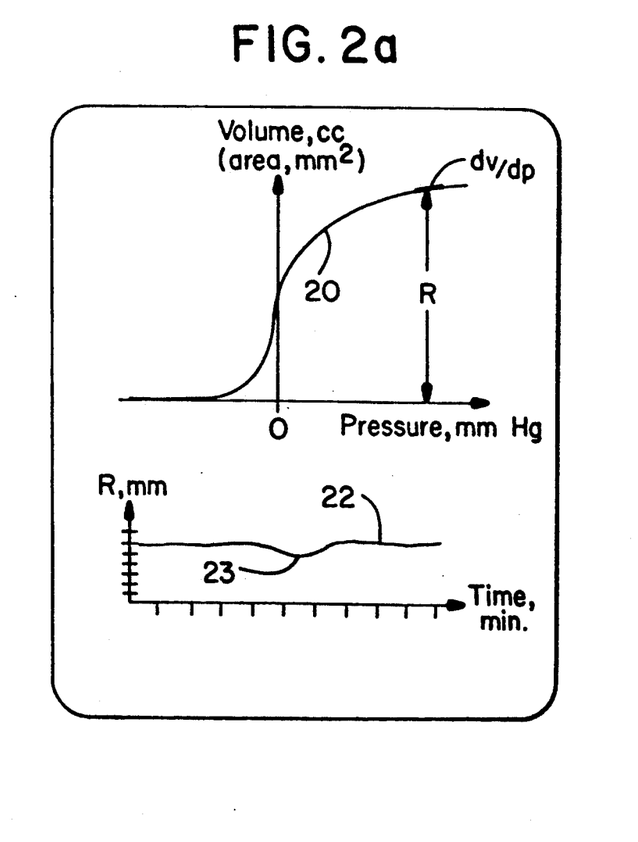
FIGS. 2a and 2b illustrate two types of vascular information displays of the instrument of FIG. 1.
Figure 2B:
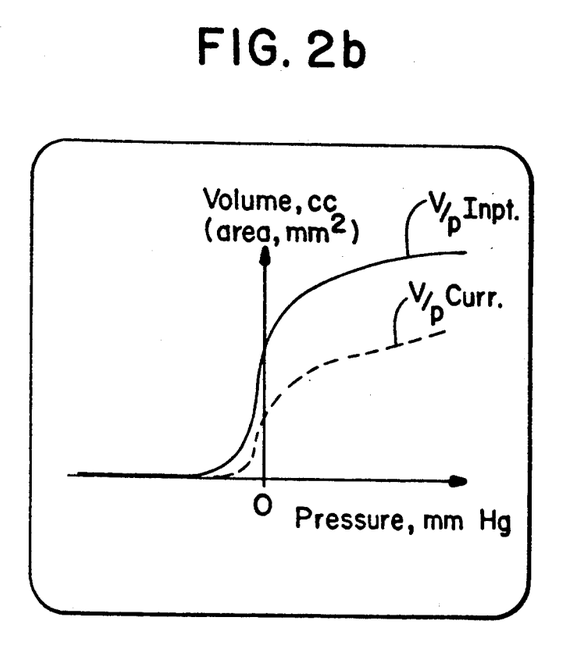

Referring first to FIG. 1, a peripheral arterial monitoring instrument constructed in accordance with the principles of the present invention is shown in use on the leg of a patient. The instrument includes a conventional blood pressure cuff 10 having a length l which is wrapped about the thigh of the patient. Although the cuff 10 may be applied to any peripheral part of the body and is most conventionally applied to the upper arm, it is preferable to use the thigh in some procedures as that is where buildups of occlusive substances leading to arteriosclerosis and the like generally first manifest themselves. In other applications the upper arm or finger may be a preferred site for application of the cuff. The cuff 10 is connected by tubing 12 to a monitor and processor 14. The monitor and processor 14 includes a number of controls for actuating and adjusting the instrument in the performance of vascular measurements including blood pressure determination. The monitor and processor also includes a display 16 where the data taken during measurements of arterial volume is displayed, either in numerical or, preferably, in graphical form as shown in FIGS. 2a and 2b. Further, the monitor and processor includes a controlled pneumatic system which controls inflation and deflation of the cuff 10 during which time measurements leading to the determination of the patient's arterial volume and compliance are taken.

FIGS. 2a and 2b illustrate several preferred techniques for displaying the information obtained through these measurements. In the upper portion of the display of FIG. 2a is a graphical display of arterial volume (or area) versus transmural pressure. As the arteries in the peripheral body part are infused with blood, the arteries expand and their volume increases as shown by the righthand portion of curve 20. The height of the righthand portion of the curve 20 also represents the effective radius of the arterial vessels R when the vessels are filled with blood. The slope of the curve 20, dV/dP, represents arterial compliance and the point at which dV/dP exhibits a maximum value is generally referred to as peak arterial compliance. Thus, the upper graph of FIG. 2a provides the physician with information as to arterial volume, compliance and effective arterial radius in the limb where the cuff is affixed.

Below the volume versus pressure graph is a graphical representation of changes in the effective arterial radius over time. This parameter may be monitored by the anesthesiologist to provide information as to bodily responses during surgery. The illustrative curve 22 of R versus time shown in the drawing is seen to be substantially flat, except at at time indicated by 23. This decrease in the R value may correlate for instance with the time at which some physical intervention such as intubation or incision is performed on the patient. If the patient is not fully anesthetized at that time, the cardiovascular system will react by contracting the arteries of the body, and the effective radius of arterial vessels will decline. Thus, the decline in curve 22 at point R would indicate to the anesthesiologist that the patient is not fully anesthetized, and further anesthetic may be required for patient comfort and safety.

FIG. 2b shows a further display of the arterial volume and compliance information which would be of assistance to an anesthesiologist. In this display volume versus pressure information is displayed before the administration of anesthesia. This curve of the patient's normal arterial volume is labelled as V/P init., the initial curve determined by the monitor and processor. As administration of the anesthetic proceeds, the patient's cardiovascular system will respond by contracting or dilating the arterial vessels. A current volume versus pressure curve is calculated periodically and displayed in correspondence with the initial curve. The current curve is labelled V/P curr. in FIG. 2b. Thus, the display of FIG. 2b provides the anesthesiologist with a continuous comparison of current arterial volume and compliance versus the patient's normal arterial volume and compliance prior to the administration of anesthetic.

Figure 3A:
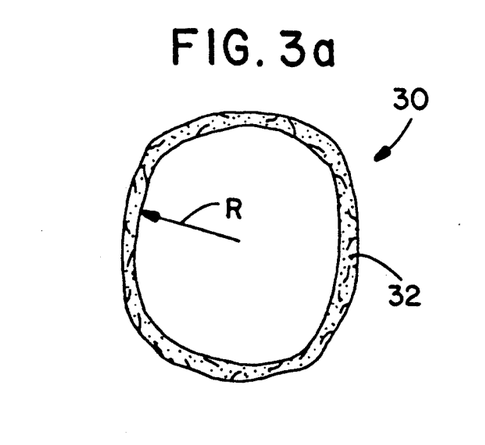
FIGS. 3a and 3b illustrate a peripheral limb of the body in relation to the information displays of FIGS. 2a and 2b.
Figure 3B:
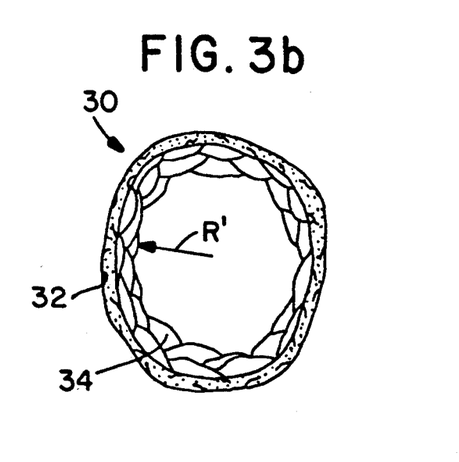

FIGS. 3a and 3b are cross-sectional illustrations of arteries showing the parameters measured by the monitor and processor 14. The R value (useful in determining or measuring arterial capacity) is the radius of an artery 30 as shown in FIG. 3a. Since the cuff encloses all arterial vessels in the portion of the limb about which it is wrapped, it will be understood that the R value is not the radius of a particular artery, but is in effect the sum of the radii of all of the arteries inside the cuff 10. Thus, the instrument provides an R value which is the effective radius taken over all arterial vessels inside the cuff.

The artery 30 is defined by the arterial wall 32. The arterial wall is composed principally of two substances, collagen and smooth muscle tissue. Collagen provides the artery with flexibility, the ability to stretch and deform. This rubber-like characteristic is one contributor to arterial compliance, and is a passive characteristic of arteries. The muscle tissue is controlled by nerves to provide stretching and deformation of the artery under control of the body's nervous system. This stretching and deformation is an active characteristic of the artery which also is a factor in arterial compliance.

Arterial volume and compliance are also affected in the case of arteriosclerosis or hardening of the arteries by the buildup of fatty substances on the inner walls of the arteries. This condition is shown in FIG. 3b, where a buildup of substances is indicated at 34 lining the wall of the artery. The ability of the artery to expand or contract under the influence of arterial muscular contraction or blood pressure changes is adversely affected by this lining of fatty substances, which can retard such motion. Since the substances also occupy a portion of the inner volume of the artery, the effective radius of the vessel R' is decreased by the presence of these substances.

It may be appreciated that if the R value for an artery or a group of arteries is known, a calculation of the cross-sectional area of the artery at that location can be performed by executing the equation $A = \pi R^2$. From this calculation of arterial area, arterial volume v may be calculated by multiplying the area by l, the length of the cuff 10 which encloses the vessels of effective area A. Thus, a measurement of V will yield a value for R, and vice versa.

Figure 4:
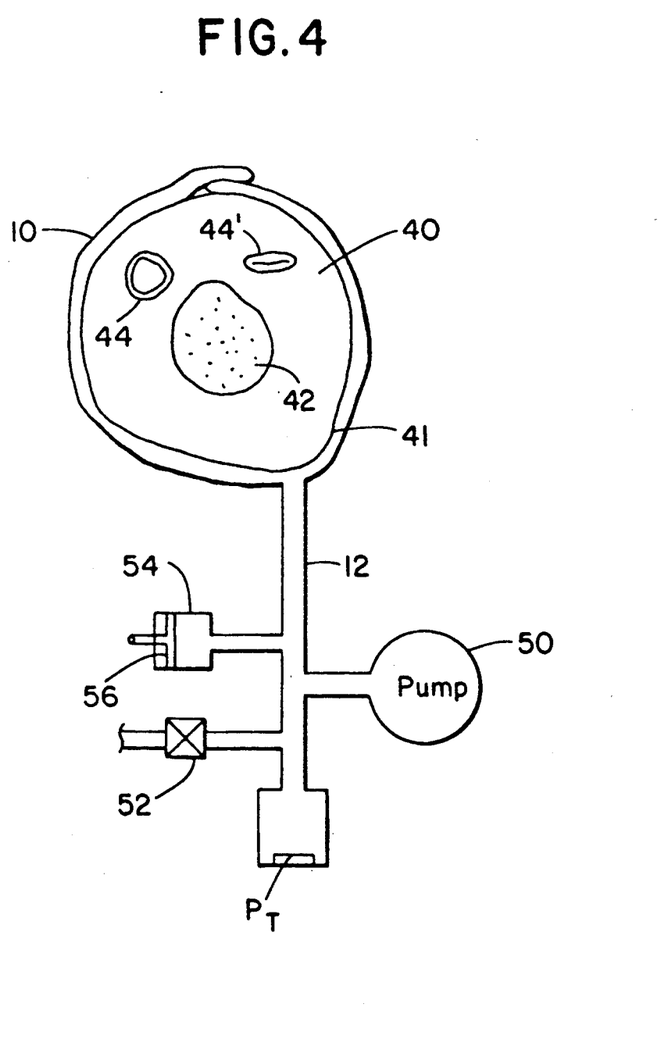
FIG. 4 illustrates schematically the connection of a arterial monitoring instrument to a limb of the body.

FIG. 4 illustrates an arrangement for taking measurements of arterial volume and compliance. Shown in FIG. 4 are a limb of the body 40 in cross-section, about which a blood pressure cuff 10 is wrappped. The skin line of the limb is indicated at 41. The cross-sectional view of the limb shows the bone 42 at the center of the limb, and an artery 44 passing through the limb. The artery 44 is shown expanded during the pumping of blood, before the cuff is applied and inflated. After inflation of the cuff to a maximal pressure, the artery will be occluded, as shown at 44'.

The cuff 10 is connected by pneumatic tubing to a pump 50. The pump 50 pumps up the cuff 10 at the start of the measurement cycle. The arrangement of FIG. 4 is modified to perform the process of the "Hartsafe Product Concept" discussed above by the inclusion of a calibration chamber 54, which is connected to the pneumatic system. As explained above, at the beginning of the inflation cycle the pump 50 is stopped and one ml of air is injected into the pneumatic system of the cuff. This may be accomplished by moving piston 56 in the chamber 54 to the right to displace one ml of air from the chamber. Given that all elements of the pneumatic system are substantially noncompliant, this one ml volume of air will compress the limb 40 by one ml. If all tissue and structure within the limb are assumed to be substantially liquid in nature and hence substantially noncompliant, the effect of the piston displacement will be to displace one ml of blood from the vascular system within the confines of the cuff. By taking pressure measurements before and after this injection of air, the process of the "Hartsafe Product Concept" calculates its calibration factor at the outset of the measurement cycle. The pump then inflates the cuff to fully occlude the arterial vessels as shown at 44', and the deflate cycle commences. During deflation, a deflation valve opens and closes to incrementally bleed air from the pneumatic system. Measurements taken by a pressure transducer $P_T$ at each pressure step are stored in correspondence with cuff pressure level and are subsequently used in a signal conditioning (processing) step at the end of the deflation cycle.

Figure 5:
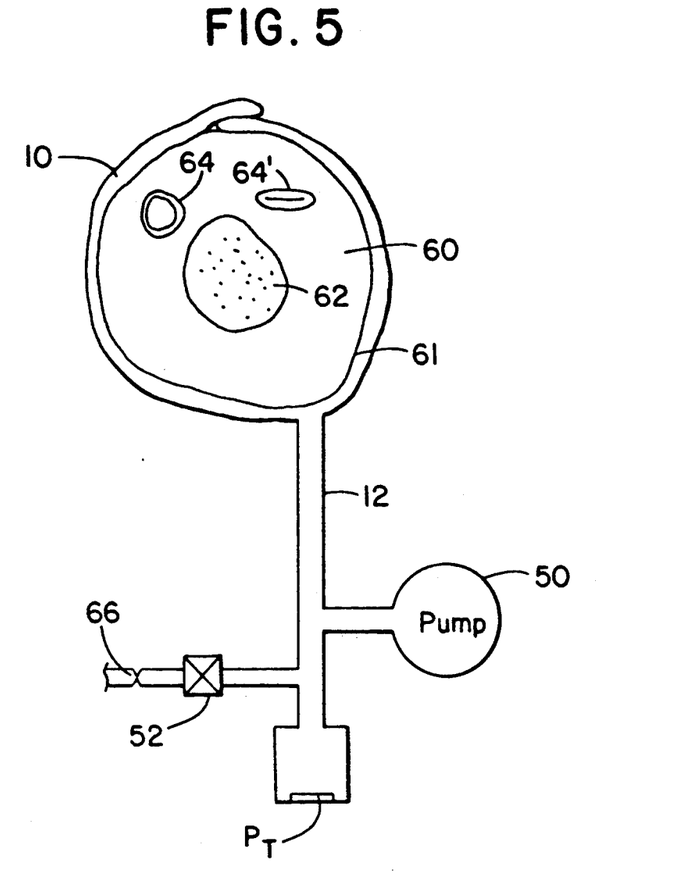
FIG. 5 is a schematic illustration of a peripheral arterial monitoring instrument of the present invention which uses an orifice for measured deflation.

The arrangement of FIG. 4 is seen to exhibit pneumatic structural, control, and operational complexity due to the inclusion of the calibration chamber 54. Furthermore, the calibration step is performed only once, at the outset of the inflation cycle. FIG. 5 illustrates a peripheral arterial volume and compliance measurement system of the present invention which obviates the need for such structural and operational complexity. In FIG. 5, the blood pressure cuff 10 is wrapped around the thigh 60 of the patient, shown in cross-section. The femur 62 is shown in the center of the thigh, and the skin line of the thigh is indicated at 61. The femoral artery is illustrated at 64 in an unoccluded condition, and in an occluded condition at 64'. The cuff 10 is connected by pneumatic tubing 12 to a pump 50, a pressure transducer $P_T$, and a deflate valve 52. An orifice 66 of predetermined cross-sectional area is located in the deflate valve outlet.

Figure 6:
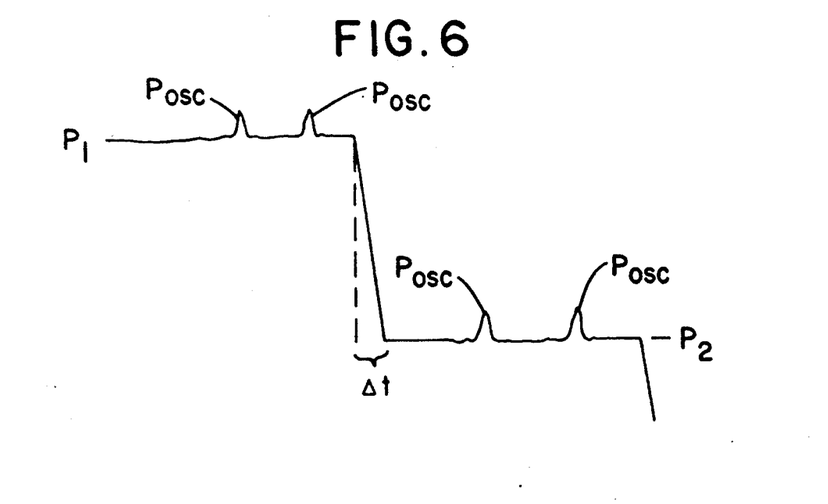
FIG. 6 is a graphical illustration of step deflation using an orifice for calibrated deflation.

In operation, the pneumatic system of FIG. 5 is operated in the conventional manner of a step-deflate automated blood pressure monitor such as the Critikon Dinamap ™ 8100. The cuff 10 is inflated by the pump 50 to a pressure which is in excess of systolic pressure, sufficient to fully occlude the artery 64'. The cuff pressure is stepped down, and the cuff pressures and oscillation pulses are recorded from the pressure transducer. Two of the pressure steps during the deflate cycle are shown in FIG. 6. The cuff pressures of the two steps are $P_1$ and $P_2$, and the oscillation pulses are shown as $P_{osc}$. The cuff pressure is stepped down in decrements of approximately 8 mm Hg. Since the air removed from the pneumatic system is expelled through an orifice of known size, the volume of air removed between each step can be calculated from a flow equation derived from the gas law $PV=nRT$, where P is pressure, V is volume, n is Avogadro's constant, R is the gas constant, and T is absolute temperature. Since the pressure on the outlet side of the orifice is ambient atmospheric pressure and the pressure on the deflate valve side of the orifice is the cuff pressure when the deflate valve is open, as measured by the pressure transducer relative to ambient pressure, the gas flow can be calculated from knowledge of the orifice size and the time during which the deflate valve is open. The time during which the deflate valve is open is shown in FIG. 6 as $\Delta t$.

Figure 9:
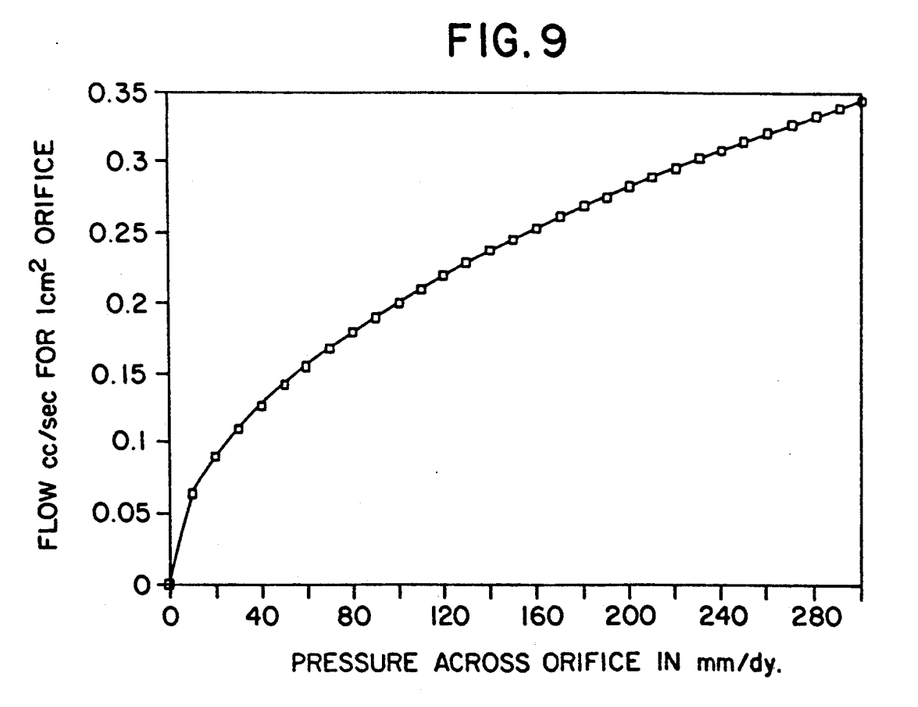
FIG. 9 is a graphical representation of flow versus pressure across the deflate orifice.

In a constructed embodiment of the present invention the flow of air from the pneumatic system is calculated from the equation $$FLOW = [(760+P)/760] \cdot [(e^{\gamma ln(760/(760+P))})^{\frac{1}{2}} - (e^{1.71 \, ln(760/(760+P))})]$$

where P is the pressure across the orifice, the number 760 is an adjustment factor for nominal barometric pressure, and $\gamma$ is an adiabatic constant. The flow through a 1 cm² orifice as a function of the pressure across the orifice during a typical deflate cycle is represented graphically in FIG. 9. Other known methods for measuring the flow of a fluid may also be employed; for instance, if the orifice in a given embodiment does not conform to theoretical models, it may be approximated empirically.

Once the FLOW has been found between each step the volume of air removed during each decrement, $\Delta V_n$, is computed from the equation $$\Delta V_n = A_{eq} \cdot FLOW_n \cdot \Delta t_n$$

where $A_{eq}$ is the equivalent area of the orifice, $FLOW_n$ is the flow rate between two pressure steps, and $\Delta t_n$ is the time during which the deflate valve was open between the two pressure steps. The FLOW is known from the preceding equation, the equivalent area of the orifice is known, and the time during which the deflate valve is open is measured by a digital clock which runs during the time that the valve is open. Since the FLOW calculation is done for each deflation step based upon the known orifice and the then extant pressure, no recalibration or modification is necessary or required for the calculated values.

Figure 10:
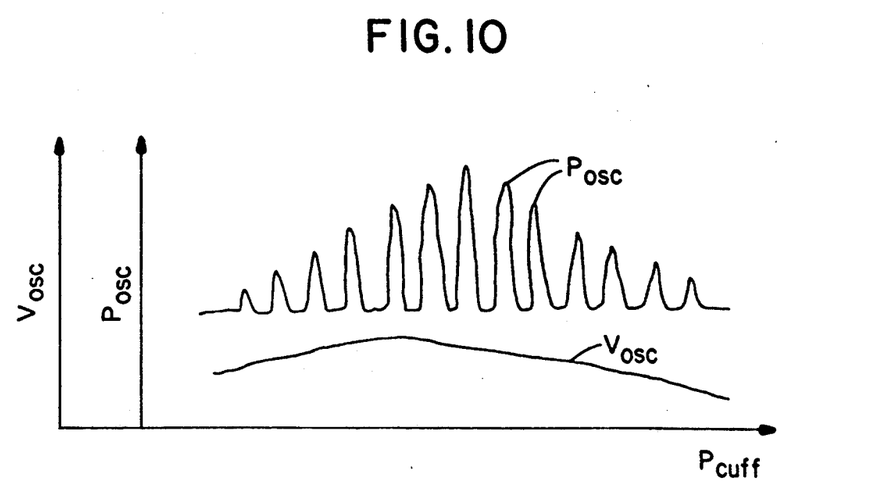
FIG. 10 is a graphical representation of oscillation pressure versus cuff pressure.

From the foregoing data a ratio can be formed of the $\Delta V_n$ values and the respective cuff pressure differentials at which they were obtained. The ratio is of the form $$\Delta V_n / \Delta P_{decr \, n}$$

where $\Delta P_{decr}$ is equal to $P_1 - P_2$ for the respective pressure step. From this ratio and the recorded values of $P_{osc}$ the volume oscillations can be calculated from the expression $$V_{osc \, n} = P_{osc \, n} \cdot \Delta V_n / \Delta P_{decr}$$

for each step decrement. The value of $P_{osc \, n}$ used for each step decrement may be the amplitude of the oscillation pulses on the $P_1$ step, the $P_2$ step, or an average of the two, due to the very small variation in oscillation pulse amplitude from one step to the next. Whichever approach is used, it is consistently applied for the full range of step values. Curves representing $V_{osc}$ and the oscillation pulses as a function of cuff pressure are illustrated in FIG. 10.

Figure 11:
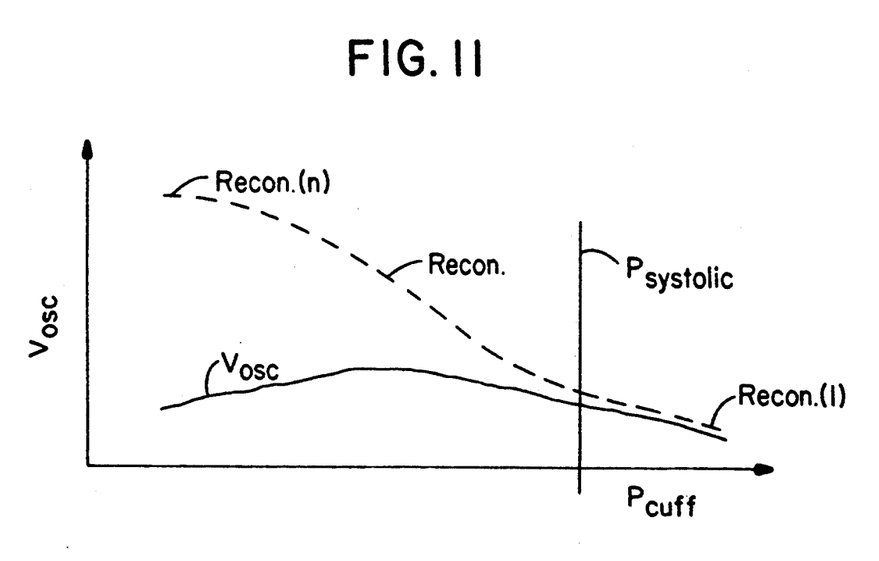
FIG. 11 is a graphical representation of volume reconstruction versus cuff pressure.

Using these volume oscillation values for the deflate cycle the arterial volume curve can now be computed in a two-step procedure. The first step is to compute a curve referred to herein as a reconstruction curve from knowledge of the $V_{osc \, n}$ values and the values of systolic and diastolic blood pressure determined by the Dinamap ™ in the conventional manner. The arterial volume curve is then computed by coordinate system transformation, by which the reconstruction curve, referenced to cuff pressure, is converted to arterial transmural pressure with reference to systolic pressure. The equation for computing the reconstruction curve is of the form $$Recon_n(P_{cuff}) = V_{osc \, n}(P_{cuff}) + Recon_n(P_{cuff} + S - D)$$

where S is systolic pressure and D is diastolic pressure and the difference of systolic-minus diastolic pressure is referred to herein as pulse pressure. It is known that $$Recon_n(P_{cuff} + S - D) = 0$$

when $(P_{cuff} + S - D)$ is greater than $P_{cuff \, max}$, where $P_{cuff \, max}$ is the maximum cuff pressure used in a particular measurement. This follows from the knowledge that at maximum cuff pressure the arteries in the limb are completely occluded. The reconstruction curve equation is seen to contain the value $Recon_n$ on both sides of the equation. Hence, the equation is solved recursively for $n=1 \ldots N$ where $1 \ldots N$ are the deflation step levels. A graphical plot of the points $Recon_n$ ($P_{cuff}$) as a function of cuff pressure is shown by the dashed curve Recon in FIG. 11 in comparison with the $V_{osc}$ curve previously shown in FIG. 10. It is seen that the plot of Recon converges with the $V_{osc}$ curve above and in the vicinity of systolic pressure.

Using the $Recon_n$ data points, the arterial volume may be calculated as a function of transmural pressure by, in effect, transforming the Recon curve about the axis of systolic pressure. The equation for performing this transformation is of the form $$P_{transmural} = \text{systolic pressure} - P_{cuff}$$

The arterial volume curve produced by this transformation is of the general shape of curve 20 of FIG. 2a and the curves of FIG. 2b.

From the data points used to plot and display the arterial volume curve, the display of FIG. 2a is readily developed. A point of reference for selection of R and dV/dP may be chosen in a number of ways. The monitor may compute mean arterial pressure in the conventional manner, and use the value of mean arterial pressure as the pressure for which R and dV/dP are chosen and displayed. Alternatively, the pressure at which dV/dP is at a maximum, peak arterial compliance, can be used as the pressure reference for selecting R and dV/dP. As a third alternative, the physician selects a transmural pressure value on the abscissa of the upper curve of FIG. 2a as the pressure for R and dV/dP. The slope of the curve at the selected pressure point can be calculated to determine arterial compliance dV/dP, and the amplitude of the volume curve at the selected pressure provides the R value.

During a surgical procedure the instrument is repeatedly actuated automatically and an R value is found each time. The R value is then displayed as a function of time as shown at the bottom of FIG. 2a. Alternatively, the volume curve calculated at the beginning of a surgical procedure is stored and continuously displayed with the most recently calculated curve in the format shown in FIG. 2b.

Another display which can be obtained from this data which would be of use to a clinician is a plot of dV/dP versus time, showing historic changes in the patient's arterial compliance during a surgical procedure. To gauge the effectiveness of a patient's cardiovascular system, another alternative is to display R (or arterial area or volume) as a function of limb size. Limb size is obtained by measuring the circumference of the limb where the cuff is attached, and entering this information into the monitor and processor 14. The ratio of this circumference (or calculated limb radius or cross-sectional area) to R (or arterial area or volume) provides an indication of cardiovascular efficiency.

Figure 7:
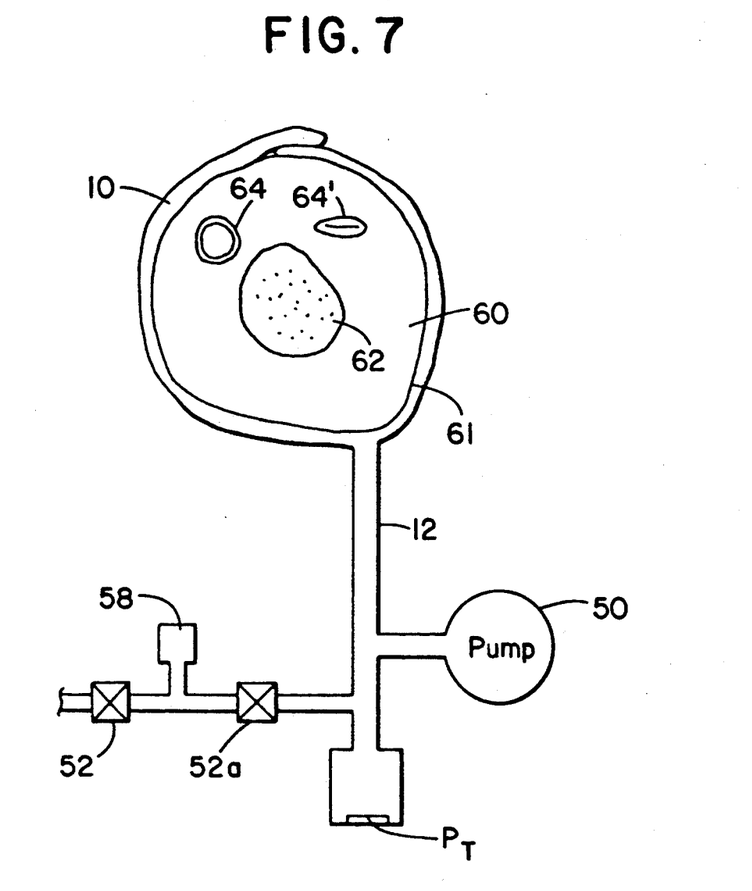
FIG. 7 is a schematic illustration of a peripheral arterial monitoring instrument of the present invention which uses a transfer volume for measured deflation.
Figure 8:
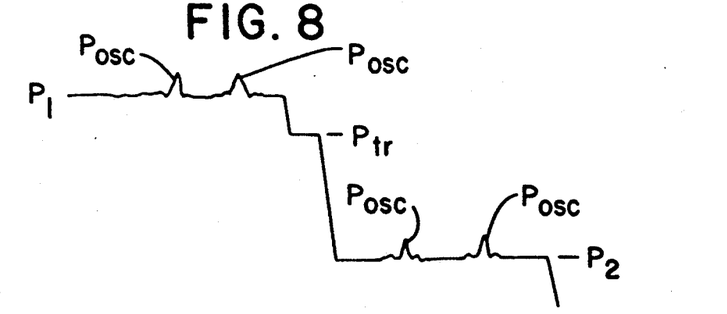
FIG. 8 is a graphical illustration of step deflation using a transfer volume for calibrated deflation.

Alternative to the orifice of FIG. 5, a flowmeter which measures the flow of expelled air could be used to provide a direct measurement of flow volume at the output of the deflate valve 52. Another alternative embodiment is to use a transfer volume of known capacity as shown in FIGS. 7 and 8. The transfer volume comprises all of the volumetric space between an intermediate dump valve 52a and the deflate valve 52. The size of the vessel indicated at 58 is chosen to provide the desired volume of the entire transfer volume. To deflate the cuff 10, the deflate valve 52 is closed after previous closure of the dump valve 52a. The air in the transfer volume between the two valves is now at atmospheric pressure. The dump valve 52a is then opened, and the transfer volume becomes pressurized to the cuff pressure, which declines to $P_{tr}$ by reason of the expansion of pressurized air into the transfer volume. From a knowledge of the previous cuff pressure $P_1$ and the new cuff pressure $P_{tr}$ as measured by the pressure transducer and the known volume of the transfer volume, $V_{tr}$, the volume of pressurized air which has been transferred into the transfer volume and removed from the cuff can be readily computed using the gas law $$\Delta V_{tr} = \Delta V_c = V_{tr}[1 - (760/(760+P_{tr}))^{1/\gamma}]$$

where $\Delta V_c$ is the volume of air removed from the cuff at pressure $P_{tr}$ and $P_{tr}$ is in mm Hg. This volume transferred bears a relationship to the pressure decrement which is $$\Delta V_{tr}/(P_1 - P_{tr})$$

which establishes a factor from which to compute the volume oscillation on a per decrement basis:

$$V_{osc\ n} = [\Delta V_{tr}/(P_1 - P_{tr})]_n \cdot P_{osc\ n}$$

The deflate valve 52 is then opened so that both valves are in the open condition. Air is expelled from the pneumatic system of the cuff and the pressure transducer is monitored until the pressure reaches the level $P_2$, at which point the dump valve 52a is closed. The deflate valve 52 is then closed, stabilizing the transfer volume at atmospheric pressure in preparation for the next step decrement. The transfer volume technique is advantageously employed to enable use of a total pressure step $P_1 - P_2$ which is conventional for a standard blood pressure monitor such as the Dinamap ™ 8100, which uses pressure step decrements of approximately 8 Mm Hg. Thus, arterial volume and compliance are obtained during the course of a normal blood pressure measurement taken by a standard automated noninvasive blood pressure monitor.

What is claimed is:

1. Instrumentation for performing measurements of arterial volume comprising:
   an inflatable cuff;
   means, connected to said cuff, for inflating and deflating said cuff;
   means for detecting pressure levels within said cuff; and
   means, coupled to said cuff inflating and deflating means, for expelling air from said cuff in a quantified manner and means for computing said quantified amount of expelled air, including means of known volume for transferring pressurized air form said cuff; and
   means responsive to said computed amounts of air for computing arterial volume.

2. Instrumentation according to claim 1, wherein said expelling means further includes a first value for selectively allowing the flow of air from said cuff into said means of known volume, and a second valve for selectively allowing the escape of air from said means of known volume.

3. Instrumentation according to claim 2, wherein said valves include actuating means for actuating said valves during a first time period during which the pressure in said cuff is reduced from a starting pressure level to an intermediate pressure level, and wherein said actuating means further actuate said valves during a second time period during which the pressure in said cuff is reduced from said intermediate pressure level to a final pressure level.

4. Instrumentation according to claim 3, wherein said first time period is a function of the volume of said means of known volume, and wherein said second time period is a function of said cuff pressure.

5. Instrumentation for performing measurements of arterial capacity comprising:
   an inflatable cuff;
   means, connected to said cuff, for inflating and deflating said cuff;
   means for detecting pressure levels within said cuff;
   means, coupled to said cuff inflating and deflating means, for expelling air from said cuff in a quantified manner and for computing said quantified amounts of expelled air; and
   means, responsive to said air expelling means and said pressure level detecting means, for computing arterial capacity.

6. Instrumentation according to claim 5, further comprising means for displaying computed arterial capacity.

7. Instrumentation for performing measurements of arterial volume comprising:
   an inflatable cuff;
   means, connected to said cuff, for inflating and deflating said cuff;
   means for detecting cuff pressure; and
   means, coupled to said cuff inflating and deflating means, for determining incremental quantities of air removed from said cuff.

8. Instrumentation according to claim 7, wherein said means for detecting cuff pressure comprises a pulse pressure sensor.

9. Instrumentation according to claim 8, wherein said pulse pressure sensor detects oscillation pulses and cuff pressure.

10. Instrumentation according to claim 7, wherein said means for determining in incremental quantities of air removed from said cuff includes an orifice of predetermined characteristics.

11. Instrumentation according to claim 10, wherein said orifice includes means for periodically coupling said cuff to said inflating and deflating means.

12. Instrumentation according to claim 7, wherein said means for determining incremental quantities of air removed from said cuff includes a volume of predetermined characteristics.

13. Instrumentation according to claim 12, further including means for coupling said volume of predetermined characteristics to said cuff by said inflating and deflating means.

* * * * *